(12) United States Patent
Ruszkay et al.

(10) Patent No.: US 7,381,675 B1
(45) Date of Patent: Jun. 3, 2008

(54) DIRECT EPOXIDATION CATALYST

(75) Inventors: Jude T. Ruszkay, Coatesville, PA (US);
Roger A. Grey, West Chester, PA (US)

(73) Assignee: Lyondell Chemical Technology, L.P., Greenville, DE (US)

( * ) Notice: Subject to any disclaimer, the term of this patent is extended or adjusted under 35 U.S.C. 154(b) by 0 days.

(21) Appl. No.: 11/641,271

(22) Filed: Dec. 19, 2006

(51) Int. Cl.
*B01J 29/06* (2006.01)
*C07C 301/00* (2006.01)

(52) U.S. Cl. .................. 502/60; 502/63; 502/64; 502/65; 502/74; 549/536; 549/533; 549/532; 549/523; 549/534

(58) Field of Classification Search .............. 502/60, 502/63, 64, 65, 74; 549/536, 533, 532, 523, 549/534
See application file for complete search history.

(56) References Cited

U.S. PATENT DOCUMENTS

| | | | |
|---|---|---|---|
| 4,285,927 A | 8/1981 | Hara et al. | |
| 4,297,241 A | 10/1981 | Kavasmaneck et al. | |
| 4,410,501 A | 10/1983 | Taramasso et al. | |
| 4,833,260 A | 5/1989 | Neri et al. | |
| 5,623,090 A | 4/1997 | Haruta et al. | |
| 6,008,388 A | 12/1999 | Dessau et al. | |
| 6,194,591 B1 * | 2/2001 | Grey et al. | 549/533 |
| 6,310,224 B1 * | 10/2001 | Grey | 549/523 |
| 6,362,349 B1 | 3/2002 | Kuperman et al. | |
| 6,403,815 B1 * | 6/2002 | Grey | 549/532 |
| 6,441,204 B1 * | 8/2002 | Grey | 549/533 |
| 6,498,259 B1 | 12/2002 | Grey et al. | |
| 6,555,493 B2 * | 4/2003 | Cooker et al. | 502/74 |
| 6,646,142 B1 | 11/2003 | Meima et al. | |
| 6,746,597 B2 | 6/2004 | Zhou et al. | |
| 6,867,312 B1 * | 3/2005 | Jubin et al. | 549/523 |

FOREIGN PATENT DOCUMENTS

| | | |
|---|---|---|
| BE | 1001038 A7 | 6/1989 |
| JP | 4-352771 | 12/1992 |

OTHER PUBLICATIONS

R. Szostak, "Non-aluminosilicate Molecular Sieves", in Molecular Sieves: Principles of Synthesis and Identification (1989) p. 205, Van Nostrand Reinhold.
G. Vayssilov, "Structural and Physicochemical Features of Titanium Silicalites" in Catal. Rev.-Sci. Eng., (1997) p. 209, vol. 39(3).
K. Engh, "Diatomite", in Kirk-Othmer Encyclopedia of Chemical Technology, online edition (2006), John Wiley & Sons, Inc.
R. Trottier et al., "Particle Size Measurement", in Kirk-Othmer Encyclopedia of Chemical Technology, online eidition (2006), John Wiley & Sons, Inc.

* cited by examiner

*Primary Examiner*—Elizabeth D. Wood
(74) *Attorney, Agent, or Firm*—Yuanzhang Han

(57) ABSTRACT

A catalyst comprising a noble metal supported on a diatomaceous earth and a transition metal zeolite is disclosed. The catalyst is used in an epoxidation process comprising reacting an olefin, hydrogen, and oxygen. The diatomaceous earth is readily available and may be used in a slurry process without further particle size enlargement.

20 Claims, No Drawings

DIRECT EPOXIDATION CATALYST

FIELD OF THE INVENTION

The invention relates to a catalyst comprising a noble metal supported on a diatomaceous earth and a transition metal zeolite. The catalyst is used to produce an epoxide by reacting an olefin, hydrogen, and oxygen.

BACKGROUND OF THE INVENTION

Direct epoxidation of higher olefins (containing three or more carbons) such as propylene with oxygen and hydrogen has been the focus of recent efforts. For example, the reaction may be performed in the presence of a catalyst comprising gold and a titanium-containing support (see, e.g., U.S. Pat. Nos. 5,623,090, 6,362,349, and 6,646,142), or a catalyst containing palladium and a titanium zeolite (see, e.g., JP 4-352771).

Mixed catalyst systems for olefin epoxidation with hydrogen and oxygen have also been disclosed. For example, Example 13 of JP 4-352771 describes the use of a mixture of titanosilicate and Pd-on-carbon for propylene epoxidation. U.S. Pat. No. 6,008,388 describes a catalyst comprising a noble metal and a titanium or vanadium zeolite, but additionally teaches that the Pd can be incorporated into a support before mixing with the zeolite. The catalyst supports disclosed include silica, alumina, and activated carbon. U.S. Pat. No. 6,498,259 discloses the epoxidation of an olefin with hydrogen and oxygen in a solvent containing a buffer in the presence of a catalyst mixture containing a titanium zeolite and a noble metal catalyst.

In a slurry epoxidation process using the mixed catalyst systems, liquid and/or gas product streams need to be separated from the solid catalyst particles. Generally it is necessary to make titanium zeolites and the supported noble metal catalyst into large enough particles (e.g., >1 μm) to make such separation (e.g., filtration) practically viable.

SUMMARY OF THE INVENTION

The invention is a catalyst comprising a noble metal supported on a diatomaceous earth and a transition metal zeolite. The catalyst is used in an epoxidation process comprising reacting an olefin, hydrogen, and oxygen. Diatomaceous earth is readily available and can be easily separated from a liquid and/or gas effluent.

DETAILED DESCRIPTION OF THE INVENTION

The invention is a catalyst comprising a transition metal zeolite. Zeolites are microporous crystalline solids with well-defined structures. Generally they contain one or more of Si, Ge, Al, B, P, or the like, in addition to oxygen. Many zeolites occur naturally as minerals and are extensively mined in many parts of the world. Others are synthetic and are made commercially for specific uses. Zeolites have the ability to act as catalysts for chemical reactions which take place mostly within the internal cavities of the zeolites. Transition metal zeolites are zeolites comprising transition metals in framework. A transition metal is a Group 3-12 element. The first row of them are from Sc to Zn. Preferred transition metals are Ti, V, Mn, Fe, Co, Cr, Zr, Nb, Mo, and W. More preferred are Ti, V, Mo, and W. Most preferred is Ti.

Preferred titanium zeolites are titanium silicates (titanosilicates). Preferably, they contain no element other than titanium, silicon, and oxygen in the lattice framework (see R. Szostak, "Non-aluminosilicate Molecular Sieves," in *Molecular Sieves: Principles of Synthesis and Identification* (1989), Van Nostrand Reinhold, pp. 205-82). Small amounts of impurities, e.g., boron, iron, aluminum, phosphorous, copper, and the like, and mixtures thereof, may be present in the lattice. The amount of impurities is preferably less than 0.5 wt. %, more preferably less than 0.1 wt. %. Preferred titanium silicates will generally have a composition corresponding to the following empirical formula: $xTiO_2 \cdot (1-x)SiO_2$, where x is between 0.0001 and 0.5000. More preferably, the value of x is from 0.01 to 0.125. The molar ratio of Si to Ti in the lattice framework of the zeolite is advantageously from 9.5:1 to 99:1, most preferably from 9.5:1 to 60:1. Particularly preferred titanium zeolites are titanium silicalites (see *Catal. Rev.-Sci. Eng.*, 39(3) (1997) 209). Examples of these include TS-1 (titanium silicalite-1, a titanium silicalite having an MFI topology analogous to that of the ZSM-5 aluminosilicate), TS-2 (having an MEL topology analogous to that of the ZSM-11 aluminosilicate), and TS-3 (as described in Belgian Pat. No. 1,001,038). Titanium zeolites having framework structures isomorphous to zeolite beta, mordenite, and ZSM-12 are also suitable for use. The most preferred is TS-1.

The catalyst comprises a noble metal. Suitable noble metals include gold, silver, platinum, palladium, iridium, ruthenium, osmium, rhenium, rhodium, and mixtures thereof. Preferred noble metals are Pd, Pt, Au, Re, Ag, and mixtures thereof. Palladium, gold, and their mixtures are particularly desirable. Typically, the amount of noble metal present in the catalyst will be in the range of from 0.01 to 20 wt. %, preferably 0.1 to 5 wt. %.

The catalyst comprises a diatomaceous earth. Diatomaceous earth, also known as kieselguhr, or diatomite, is a naturally occurring, highly structured, fine hydrous silica powder made up of the remains of planktonic algae. Many different types of diatomaceous earth are available commercially. Diatomaceous earth is used in many applications as the uniquely porous nature of each particle gives diatomite high surface area, low bulk density, high permeability, high water absorption, and low abrasion. Diatomaceous earth filter aids are used to prevent blinding of filter elements and are used to clarify liquids in brewing, water treatment, wine making, sugar refining, fruit juice production, and in industrial chemicals processing. Diatomaceous earth functional fillers are used in paints, rubber, plastics, pharmaceuticals, toothpastes, polishes, and chemicals where performance is improved by the unique properties of diatomaceous earth. Diatomaceous earth can also be used as catalyst support. See Kenneth R. Engh, "Diatomite," *Kirk-Othmer Encyclopedia of Chemical Technology* online edition, 2006. See also U.S. Pat. Nos. 4,297,241, 4,285,927, and 6,746,597

Diatomaceous earth gives many advantages as a catalyst or a catalyst support. First, diatomaceous earth is easy to filter. When a solid catalyst is used in a slurry reaction, it is usually necessary to separate the catalyst from a liquid and/or gas reaction effluent. In a continuous slurry reaction, a liquid and/or gas effluent needs to be continuously withdrawn from the reactor. In either case, the ease of filtration improves the operation. Second, commercially available diatomaceous earth materials can be used in slurry reactions without the need of particle enlargement. For example, diatomaceous earth materials available from EaglePicher Filtration & Minerals, Inc. have median particle sizes of 10-80 μm (Technical Data Sheet, http://www.eaglepicher.com). In comparison, other catalyst supports (e.g., silica, alumina, and titania) would generally need to be processed (e.g., spray-dried) to obtain particles of such sizes.

The noble metal is supported on the diatomaceous earth. The manner in which the noble metal is incorporated in a diatomaceous earth is not critical. For example, the noble metal may be supported on the diatomaceous earth by impregnation, ion-exchange, adsorption, precipitation, or the like.

There are no particular restrictions regarding the choice of the noble metal compound or complex used as the source of the noble metal. Suitable compounds include nitrates, sulfates, halides (e.g., chlorides, bromides), carboxylates (e.g., acetate), and amine or phosphine complexes of noble metals (e.g., palladium(II) tetraammine bromide, tetrakis(triphenylphosphine) palladium(0)).

Similarly, the oxidation state of the noble metal is not critical. Palladium, for instance, may be in an oxidation state anywhere from 0 to +4 or any combination of such oxidation states. To achieve the desired oxidation state or combination of oxidation states, the noble metal compound after being introduced on the diatomaceous earth may be fully or partially pre-reduced. Satisfactory catalytic performance can, however, be attained without any pre-reduction.

The weight ratio of the transition metal zeolite to noble metal is not particularly critical. However, a transition metal zeolite to noble metal weight ratio of from 10:1 to 5000:1 (grams of transition metal zeolite per gram of noble metal) is preferred.

The catalyst may comprise a promoter. A promoter helps to improve the catalyst performance (e.g., activity, selectivity, life of the catalyst). Preferred promoters include lead, zinc, alkaline earth metals, lanthanide metals, and the like. Lead is particularly preferred. The promoter may be added on the transition metal zeolite and/or the diatomaceous earth. Preferably it is added to the diatomaceous earth. While the choice of compound used as the promoter source is not critical, suitable compounds include metal carboxylates (e.g., acetate), halides (e.g., chlorides, bromides, iodides), nitrates, sulfate, and the like. The typical amount of promoter metal present in the catalyst will be in the range of from about 0.001 to 5 weight percent, preferably 0.001 to 2 weight percent relative to the catalyst.

When the catalyst is used in a slurry, the diatomaceous earth has preferably a mass median particle size in the range of 1 to 200 µm, more preferably in the range of 10 to 100 µm. The mass median particle diameter is the diameter that divides half of the mass ("Particle Size Measurement," *Kirk-Othmer Encyclopedia of Chemical Technology* online edition, 2006).

The invention also includes an epoxidation process comprising reacting an olefin, hydrogen, and oxygen in the presence of the catalyst of the invention.

An olefin is used in the process. Suitable olefins include any olefin having at least one carbon-carbon double bond, and generally from 2 to 60 carbon atoms. Preferably the olefin is an acyclic alkene of from 2 to 30 carbon atoms; the process is particularly suitable for epoxidizing $C_2$-$C_6$ olefins. More than one double bond may be present in the olefin molecule, as in a diene or triene. The olefin may be a hydrocarbon or may contain functional groups such as halogen, carboxyl, hydroxyl, ether, carbonyl, cyano, or nitro groups, or the like. In a particularly preferred process, the olefin is propylene and the epoxide is propylene oxide.

Oxygen and hydrogen are required. Although any sources of oxygen and hydrogen are suitable, molecular oxygen and molecular hydrogen are preferred. The molar ratio of hydrogen to oxygen can usually be varied in the range of $H_2:O_2=1:100$ to 5:1 and is especially favorable at 1:5 to 2:1. The molar ratio of oxygen to olefin is usually 1:1 to 1:20, and preferably 1:1.5 to 1:10. Relatively high oxygen to olefin molar ratios (e.g., 1:1 to 1:3) may be advantageous for certain olefins.

In addition to the olefin, oxygen, and hydrogen, an inert gas is preferably used in the process. Any desired inert gas can be used. Suitable inert gases include nitrogen, helium, argon, and carbon dioxide. Saturated hydrocarbons with 1-8, especially 1-6, and preferably 1-4 carbon atoms, e.g., methane, ethane, propane, and n-butane, are also suitable. Nitrogen and saturated $C_1$-$C_4$ hydrocarbons are preferred inert gases. Mixtures of inert gases can also be used. The molar ratio of olefin to gas is usually in the range of 100:1 to 1:10 and especially 20:1 to 1:10.

The process may be performed in a continuous flow, semi-batch, or batch mode. A continuous flow process is preferred. The catalyst is preferably in a slurry or a fixed bed. For a fixed-bed process, the catalyst is preferably formed into extrudates, tablets, granules, and the like.

It is advantageous to work at a pressure of 1-200 bars. The process is carried out at a temperature effective to achieve the desired olefin epoxidation, preferably at temperatures in the range of 0-200° C., more preferably, 20-150° C. Preferably, at least a portion of the reaction mixture is a liquid under the reaction conditions.

A reaction solvent is preferably used in the process. Suitable reaction solvents are liquid under the reaction conditions. They include, for example, oxygen-containing hydrocarbons such as alcohols, aromatic and aliphatic solvents such as toluene and hexane, nitriles such as acetonitrile, carbon dioxide, and water. Suitable oxygenated solvents include alcohols, ethers, esters, ketones, carbon dioxide, water, and the like, and mixtures thereof. Preferred oxygenated solvents include water and lower aliphatic $C_1$-$C_4$ alcohols such as methanol, ethanol, isopropanol, tert-butanol, and mixtures thereof. Fluorinated alcohols can be used.

Where a reaction solvent is used, it may be advantageous to use a buffer. The buffer is employed in the reaction to inhibit the formation of glycols or glycol ethers during the epoxidation, and it can improve the reaction rate and selectivities. The buffer is typically added to the solvent to form a buffer solution, or the solvent and the buffer are added separately. Useful buffers include any suitable salts of oxyacids, the nature and proportions of which in the mixture are such that the pH of their solutions preferably ranges from 3 to 12, more preferably from 4 to 10, and most preferably from 5 to 9. Suitable salts of oxyacids contain an anion and a cation. The anion may include phosphate, carbonate, bicarbonate, sulfate, carboxylates (e.g., acetate), borate, hydroxide, silicate, aluminosilicate, or the like. The cation may include ammonium, alkylammonium (e.g., tetraalkylammoniums, pyridiniums), alkylphosphonium, alkali metal, and alkaline earth metal ions, or the like. Examples include $NH_4$, $NBu_4$, $NMe_4$, Li, Na, K, Cs, Mg, and Ca cations. The preferred buffer comprises an anion selected from the group consisting of phosphate, carbonate, bicarbonate, sulfate, hydroxide, and acetate; and a cation selected from the group consisting of ammonium, alkylammonium, alkylphosphonium, alkali metal, and alkaline earth metal ions. Buffers may preferably contain a combination of more than one suitable salt. Typically, the concentration of the buffer in the solvent is from 0.0001 M to 1 M, preferably from 0.0005 M to 0.3 M. The buffer may include ammonium hydroxide which can be formed by adding ammonia gas to the reaction system. For instance, one may use a pH=12-14 solution of ammonium hydroxide to balance the pH of the reaction system. More preferred buffers include alkali metal phosphates, ammonium phosphate, and ammonium hydroxide. The ammonium phosphate buffer is particularly preferred.

Following examples merely illustrate the invention. Those skilled in the art will recognize many variations that are within the spirit of the invention and scope of the claims.

EXAMPLE 1

Pd—Au on FN-1, Calcined 300° C. (Catalyst A)

Diatomaceous earth FN-1 (EaglePicher Filtration and Minerals, Inc., 30 g) is added to a solution made from deionized water (120 g), aqueous sodium tetrachloroaurate solution (20.74 wt. % gold, 0.795 g), and disodium tetrachloropalladate (from Aldrich Chemical, 0.825 g). Sodium bicarbonate powder is added to the slurry until the pH reaches 7.24. The slurry is allowed to react for 4 h at 50° C., then filtered. The solid is washed with deionized water (7×80 g). The solid is then calcined in air at 110° C. for 4 h (10° C./min from room temperature to 110° C.) and at 300° C. for 4 h (2° C./min from 110° C. to 300° C.). The calcined solid is then transferred to a quartz tube and treated with a gas containing 4 vol. % hydrogen in nitrogen at 100° C. for 1 h (flow rate 100 mL/h) and then purged with nitrogen for 1 h. The final solid (Catalyst A) contains 1.0 wt. % palladium and 0.44 wt. % gold.

EXAMPLE 2

Pd—Au on FN-1, Calcined 550° C. (Catalyst B)

The procedure of Example 1 is repeated except that the solid is calcined at 550° C. before hydrogen reduction. The solid obtained (Catalyst B) contains 1.0 wt. % palladium and 0.44 wt. % gold.

EXAMPLE 3

Pd—Au on FN-1, Calcined 650° C. (Catalyst C)

The procedure of Example 1 is repeated except that the solid is calcined at 650° C. before hydrogen reduction. The solid obtained (Catalyst C) contains 1.0 wt. % palladium and 0.44 wt. % gold.

EXAMPLE 4

Pd—Au on FP-3, Calcined 300° C. (Catalyst D)

The procedure of Example 1 is repeated except that diatomaceous earth FP-3 (EaglePicher Filtration and Minerals, Inc., 30 g) is used instead of FN-1. The solid obtained (Catalyst D) contains 0.75 wt. % palladium and 0.35 wt. % gold.

EXAMPLE 5

Pd—Au on FP-3, Calcined 550° C. (Catalyst E)

The procedure of Example 4 is repeated except that the solid is calcined at 550° C. before hydrogen reduction. The solid obtained (Catalyst E) contains 0.75 wt. % palladium and 0.35 wt. % gold.

EXAMPLE 6

Pd—Au on FW-14, Calcined 300° C. (Catalyst F)

The procedure of Example 1 is repeated except that diatomaceous earth FW-14 (EaglePicher Filtration and Minerals, Inc., 30 g) is used instead of FN-1. The solid obtained (Catalyst F) contains 0.81 wt. % palladium and 0.33 wt. % gold.

COMPARATIVE EXAMPLE 7

Pd—Au on Titania (Catalyst G)

A spray-dried anatase (average diameter 35 μm, air calcined at 700° C. for 4 h, surface area 40 m$^2$/g, 20 g) is added to a solution made from deionized water (80 g), an aqueous sodium tetrachloroaurate solution (20.74 wt. % gold, 0.53 g), and disodium tetrachloropalladate (19.75 wt. % Pd, 1.01 g). Sodium bicarbonate powder is added to the slurry until the pH reaches 7.24. The slurry is allowed to react for 4 h at 50° C., then filtered. The solid is washed with deionized water (7×80 g). The solid is then calcined in air at 110° C. for 4 h (at a rate of 10° C./min from room temperature to 110° C.) and at 550° C. for 4 h (at a rate of 2° C./min from 110° C. to 550° C.). The calcined solid is transferred to a quartz tube and treated with a gas containing 4 vol. % hydrogen in nitrogen at 100° C. for 1 h (flow rate 100 mL/h) and then purged with nitrogen for 1 h. The final solid (Catalyst G) contains 1.0 wt. % palladium and 0.42 wt. % gold.

EXAMPLE 8

Propylene Epoxidation with Catalyst A

Titanium silicalite-1 (TS-1) is prepared by following procedures disclosed in U.S. Pat. Nos. 4,410,501 and 4,833,260, and calcined in air at 550° C.

An ammonium phosphate buffer solution (0.1 M, pH 6) is prepared as follows. Ammonium dihydrogen phosphate (11.5 g) is dissolved in deionized water (900 g). Aqueous ammonium hydroxide (30 wt. % NH$_4$OH) is added to the solution until the pH reads 6 via a pH meter. The volume of the solution is then increased to exactly 1000 mL with additional deionized water.

A 300-mL stainless steel reactor is charged with Catalyst A (0.07 g), TS-1 powder (0.63 g), the buffer solution prepared above (13 g), and methanol (100 g). The reactor is then charged to 300 psig with a feed gas consisting of 2 volume percent (vol. %) hydrogen, 4 vol. % oxygen, 5 vol. % propylene, 0.5 vol. % methane, and the balance nitrogen. The pressure in the reactor is maintained at 300 psig via a back pressure regulator with the feed gases pass continuously through the reactor at 1600 mL/min (measured at 23° C. and 1 atmosphere pressure). In order to maintain a constant solvent level in the reactor during the run, the oxygen, nitrogen and propylene feeds are passed through a 2-L stainless steel vessel (saturator) preceding the reactor containing 1.5 L of methanol. The reaction mixture is heated to 60° C. while it is stirred at 1500 rpm. The gaseous effluent is analyzed by an online gas chromatograph (GC) every hour. The liquid is analyzed by offline GC at the end of the 18 h run. The products formed include propylene oxide (PO), propane, and derivatives of propylene oxide such as propylene glycol, propylene glycol monomethyl ethers, dipropylene glycol, and dipropylene glycol methyl ethers. The calculated results are shown in Table 1. The catalyst productivity is defined as the grams of PO formed (including PO which is subsequently reacted to form PO derivatives) per gram of catalyst per hour. POE (mole)=moles of PO+moles of PO units in the PO derivatives. PO/POE= (moles of PO)/(moles of POE)×100. Propylene to POE selectivity=(moles of POE)/(moles of propane formed+ moles of POE)×100.

EXAMPLES 9-14

Propylene Epoxidation with Catalysts B, C, D, E, F, G

The procedure of Example 8 is repeated except that Catalysts B, C, D, E, F, G are used respectively instead of Catalyst A. Results are shown in Table 1.

TABLE 1

| | Epoxidation of Propylene | | | | | | |
|---|---|---|---|---|---|---|---|
| Example | 8 | 9 | 10 | 11 | 12 | 13 | 14 |
| Pd—Au Catalyst | A | B | C | D | E | F | G |
| Support | FN-1 | FN-1 | FN-1 | FP-3 | FP-3 | FW-14 | Anatase |
| Support Surface Area ($m^2/g$) | 24 | 24 | 24 | 2 | 2 | 0.4 | 28 |
| Calcination Temperature (° C.) | 300 | 550 | 650 | 300 | 550 | 300 | 550 |
| Catalyst Productivity, g POE/g cat/h | 0.57 | 0.49 | 0.46 | 0.46 | 0.43 | 0.43 | 0.47 |
| PO/POE, % (mole/mole) | 88 | 90 | 91 | 90 | 90 | 91 | 90 |
| Propylene to POE Selectivity, % (mole/mole) | 56 | 77 | 84 | 63 | 75 | 65 | 80 |
| Hydrogen to POE Selectivity, % (mole/mole) | 18 | 23 | 27 | 25 | 29 | 21 | 34 |
| Oxygen to POE Selectivity, % (mole/mole) | 37 | 45 | 43 | 38 | 42 | 31 | 38 |

We claim:

1. A catalyst comprising a noble metal supported on a diatomaceous earth and a transition metal zeolite.

2. The catalyst of claim 1 wherein the transition metal zeolite is a titanium zeolite.

3. The catalyst of claim 1 wherein the transition metal zeolite is TS-1.

4. The catalyst of claim 1 wherein the noble metal is selected from the group consisting of gold, silver, platinum, palladium, iridium, ruthenium, osmium, and mixtures thereof.

5. The catalyst of claim 1 wherein the noble metal is palladium, gold, or a palladium-gold mixture.

6. The catalyst of claim 1 wherein the diatomaceous earth has a mass median diameter from 1 to 200 μm.

7. The catalyst of claim 1 wherein the diatomaceous earth has a mass median diameter from 10 to 100 μm.

8. An epoxidation process comprising reacting an olefin, hydrogen, and oxygen in the presence of the catalyst of claim 1.

9. The process of claim 8 wherein the transition metal zeolite is a titanium zeolite.

10. The process of claim 8 wherein the transition metal zeolite is TS-1.

11. The process of claim 8 wherein the noble metal is selected from the group consisting of gold, silver, platinum, palladium, iridium, ruthenium, osmium, and mixtures thereof.

12. The process of claim 8 wherein the noble metal is palladium, gold, or a palladium-gold mixture.

13. The process of claim 8 wherein the diatomaceous earth has a mass median diameter from 1 to 200 μm.

14. The process of claim 8 wherein the diatomaceous earth has a mass median diameter from 10 to 100 μm.

15. The process of claim 8 performed in a slurry.

16. The process of claim 8 performed in a fixed bed.

17. The process of claim 8 performed in a continuous mode.

18. The process of claim 8 performed in the presence of a solvent.

19. The process of claim 18 performed in the presence of a buffer.

20. The process of claim 8 wherein the olefin is propylene.

* * * * *